(12) United States Patent
Mehta et al.

(10) Patent No.: US 11,918,684 B2
(45) Date of Patent: Mar. 5, 2024

(54) PHARMACEUTICAL COMPOSITION OF ORAL SUSPENSION OF IMMUNOSUPPRESSIVE AGENTS

(71) Applicant: LIQMEDS WORLDWIDE LIMITED, Middlesex (GB)

(72) Inventors: Sandip Mehta, Ahmedabad (IN); Manish Umrethia, Ahmedabad (IN); Henil Patel, Ahmedabad (IN); Jayanta Kumar Mandal, Ahmedabad (IN)

(73) Assignee: LIQMEDS WORLDWIDE LIMITED, Hayes (GB)

( * ) Notice: Subject to any disclaimer, the term of this patent is extended or adjusted under 35 U.S.C. 154(b) by 0 days.

(21) Appl. No.: 16/494,030

(22) PCT Filed: Mar. 12, 2018

(86) PCT No.: PCT/IB2018/051597
§ 371 (c)(1),
(2) Date: Sep. 13, 2019

(87) PCT Pub. No.: WO2018/167628
PCT Pub. Date: Sep. 20, 2018

(65) Prior Publication Data
US 2020/0246261 A1   Aug. 6, 2020

(30) Foreign Application Priority Data
Mar. 13, 2017   (IN) .............. 201721008648

(51) Int. Cl.
| A61K 9/00 | (2006.01) |
| A61K 9/10 | (2006.01) |
| A61K 47/02 | (2006.01) |
| A61K 47/10 | (2017.01) |
| A61K 47/14 | (2017.01) |
| A61K 47/26 | (2006.01) |
| A61K 47/36 | (2006.01) |

(52) U.S. Cl.
CPC .......... *A61K 9/0095* (2013.01); *A61K 9/0053* (2013.01); *A61K 9/10* (2013.01); *A61K 47/02* (2013.01); *A61K 47/10* (2013.01); *A61K 47/14* (2013.01); *A61K 47/26* (2013.01); *A61K 47/36* (2013.01)

(58) Field of Classification Search
CPC ...... A61K 9/0095; A61K 9/0053; A61K 9/10; A61K 47/02; A61K 47/10; A61K 47/14; A61K 47/26; A61K 47/36
See application file for complete search history.

(56) References Cited

U.S. PATENT DOCUMENTS

| 4,788,220 A | 11/1988 | Mody et al. |
| 5,272,137 A | 12/1993 | Blase et al. |
| 5,688,529 A * | 11/1997 | Lidgate ............ A61P 29/00 424/489 |
| 2006/0235070 A1 * | 10/2006 | Hayden ............ A61K 45/06 514/460 |
| 2007/0208069 A1 | 9/2007 | Krishnan et al. |
| 2008/0260837 A1 | 10/2008 | Namburi et al. |
| 2011/0166225 A1 | 7/2011 | Verma et al. |
| 2013/0005722 A1 * | 1/2013 | Senapati ............ A61K 47/36 514/233.5 |
| 2014/0371242 A1 * | 12/2014 | Wang ............ A61K 31/52 514/263.2 |
| 2015/0108033 A1 * | 4/2015 | Vamvakas ............ A61K 9/4866 424/452 |
| 2016/0089437 A1 | 3/2016 | Hsiao |
| 2016/0228379 A1 * | 8/2016 | Kumar ............ A61K 47/36 |
| 2016/0271070 A1 | 9/2016 | Singh et al. |
| 2016/0287594 A1 | 10/2016 | Gupta et al. |
| 2017/0035774 A1 | 2/2017 | Toti et al. |
| 2020/0246261 A1 | 8/2020 | Mehta et al. |

FOREIGN PATENT DOCUMENTS

| EP | 2497467 A1 | 9/2012 |
| IN | 201621039392 A | 5/2018 |
| WO | 2002094220 A1 | 11/2002 |
| WO | 2009082038 A2 | 7/2009 |

(Continued)

OTHER PUBLICATIONS

Kennedy et al. Stability of cyclophosphamide in extemporaneous oral suspensions. Ann. Pharmacother. 2010; 44(2):295-301. (Year : 2010).*
Reding et al. Efficacy and pharmacokinetics of tacrolimus oral suspension in pediatric liver transplant recipients. Pediatr. Transplant 2002, 6(2):124-126. (Year: 2002).*
Anaizi et al., Stability of mycophenolate mofetil in an extemporaneously compounded oral liquid, Am. J. Health Syst. Pharm. (1998) 55(9): 926-929.
Venkataramanan et al., Stability of Mycophenolate Mofetil as an Extemporaneous Suspension, Ann. Pharmacother. (1998) 32(7-8): 755-757.
Swenson et al. Stability of mycophenolate mofetil in an extemporaneously compounded sugar-free oral liquid, Am J Health Syst Pharm (1999) 56(21): 2224-2226.

(Continued)

*Primary Examiner* — Robert A Wax
*Assistant Examiner* — Olga V. Tcherkasskaya
(74) *Attorney, Agent, or Firm* — Merchant & Gould P.C.; Daniel R. Evans

(57) ABSTRACT

The present invention provides pharmaceutical composition of immunosuppressive agent in oral suspension dosage form. The oral suspension composition comprises of immunosuppressive agent with other pharmaceutical excipients such as vehicle, suspending agent, solvent or cosolvent, preservative, sweetener, antifoaming agent, wetting agent, buffering agent and flavouring agent. The present invention oral suspension having improved stability, palatability with high dose of active ingredient. The present invention provides oral suspension with flavor that has masked bitter taste of the drug and eliminates difficulty of administration. Further, the present invention also provides a convenient, easy process for preparation thereof.

3 Claims, No Drawings

(56) References Cited

FOREIGN PATENT DOCUMENTS

| WO | 2009108828 A2 | 9/2009 |
| WO | 2018067401 A1 | 4/2018 |
| WO | 2018167628 A1 | 9/2018 |
| WO | 2019038584 A1 | 2/2019 |

OTHER PUBLICATIONS

Ensom et al., Stability of Mycophenolate Mofetil in a 1:1 Mixture of Ora-Sweet and Ora-Plus, CJHP (2002) 55(1): 63-65.
Fahimi et al., Physical and Chemical Stability of Mycophenolate Mofetil (MMF) Suspension Prepared at the Hospital, Iran J Pharm Res. (2012) 11(1): 171-175.
International Search Report for PCT/IB2019/000987 (dated Feb. 21, 2020).
Co-pending U.S. Appl. No. 18/362,179, filed Jul. 31, 2023 Entitled "Pharmaceutical Suspension for Oral Dosage," Mehta, et al.
U.S. Office Action dated Sep. 28, 2023 cited in U.S. Appl. No. 18/362,179 (8 pages).

* cited by examiner

PHARMACEUTICAL COMPOSITION OF ORAL SUSPENSION OF IMMUNOSUPPRESSIVE AGENTS

This application is the U.S. national stage application of International Patent Application No. PCT/IB2018/051597, filed on Mar. 12, 2018, which claims priority to Indian Patent Application No. 201721008648, filed on Mar. 13, 2017.

FIELD OF THE INVENTION

The present invention relates to the oral liquid pharmaceutical composition of immunosuppressive agents. More particularly, the present invention relates to oral suspension composition comprises of immunosuppressive agent with improved stability and palatability with high dose of active ingredient.

BACKGROUND OF THE INVENTION

Immunosuppressive are medications that help to suppress the immune system. Typically they are used in patients who received organ transplants to help and prevent their bodies from rejecting the transplanted organ. Also immunosuppressant drugs are used to treat autoimmune diseases. With an autoimmune disease, the immune system attacks the body's own tissue. Because immunosuppressant drugs weaken the immune system, they suppress this reaction. This helps reduce the impact of the autoimmune disease on the body.

Person who undergoes an organ transplant surgery must take immunosuppressant drugs as immune system of the person sees a transplanted organ as a foreign mass. As a result, immune system attacks the organ as it would attack any foreign cell. This can cause severe damage and lead to reject the transplanted organ. Immunosuppressant drugs weaken immune system to reduce body's reaction to the foreign organ. Thus, the drugs allow the transplanted organ to remain healthy and free from damage.

Important immunosuppressive agents include azathioprine, mycophenolate mofetil, cyclosporine, fingolimod, methotrexate, leflunomide, cyclophosphamide, chlorambucil, nitrogen mustard, tacrolimus and sirolimus.

CN1919184 discloses pharmaceutical formulations of an immunosuppressant dispersible tablets and process for preparation thereof.

EP0724581 relates to a pharmaceutical composition for preparing an aqueous intravenous formulation of an immunosuppressive mycophenolatemofetil.

CN101185623 relates to oral pharmaceutical composition in dry suspension dosage form comprises mycophenolatemofetil, filler, sweeteners, suspending agent and wetting agent.

U.S. Pat. No. 4,753,935 discloses oral suspension of an immunosuppressive agent mycophenolatemofetil. But this composition comprises the drug relatively low dose of 1 gram of active ingredient in 100 ml.

Currently available preparations of immunosuppressive agents are generally given orally in solid dosage forms of tablets or capsules, dry suspension or injections. The oral liquid dosage is more patient compliance as solid dosage form is not convenient for all patients to swallow. Further, immunosuppressive agents have strong bitterness that results a bitter taste and a feeling of numbness in the mouth. Injection dosage is also not convenient when the drug is needed to administer in high dose for more than once per day. Further, administration of injectable products either require hospitalization or medical staff.

Patients undergone organ transplant, they cannot take immunosuppresants in a solid dosage forms orally for 24-72 hr, so they are being treated with injectable immunosuppresants.

Hence, there is a need for development of oral liquid dosage form that is stable, having high bioavailability and palatability with patient compliance as well as can be administered with tube directly in to gastro-intestinal tract.

The present invention is directed to flavored liquid suspension composition of immunosuppressive agents that has masked bitter taste of active ingredient. Further, currently inventive formulation is exhibiting improved stability and palatability with high dose of active ingredient.

Objects of the Invention

The main object of the present invention is to provide oral pharmaceutical suspension of immunosuppressive agent with improved stability and palatability with high dose of active ingredient.

Another object of the present invention is to provide oral suspension of immunosuppressive agent with flavor that has masked bitter taste of the active ingredient and having patient compliance that eliminates difficulty of administration.

Another object of present invention is to provide oral suspension having dose accuracy, flexibility and uniformity of dosage.

Still another object of the present invention is to provide a convenient process for preparation of oral pharmaceutical suspension of immunosuppressive agent.

SUMMARY OF THE INVENTION

The present invention relates to an oral pharmaceutical suspension of an immunosuppressive agent with improved stability, palatability with high dose of active ingredient. The present invention provides oral pharmaceutical suspension of an immunosuppressive agent with flavor that has masked unpleasant taste of the drug and patient compliance that eliminates difficulty of administration.

Another aspect of the present invention relates to oral suspension of an immunosuppressive agent that comprises an active ingredient with other pharmaceutically acceptable excipients such as vehicle, suspending agent, solvent or cosolvent, preservative, sweetener, antifoaming agent, wetting agent, buffering agent and flavouring agent. The present invention also provides a process for preparation thereof.

DETAILED DESCRIPTION OF THE INVENTION

Immunosuppressant agents are anti-rejection drug used to prevent the body from rejecting a transplanted organ.

Immunosuppressant drugs greatly decrease the risks of rejection and protecting the new organ and preserving its function. These drugs act by blocking the immune system so that it is less likely to react against the transplanted organ. A wide variety of drugs are available to achieve this aim to reduce the risk of rejection.

The present invention relates to an oral pharmaceutical suspension of immunosuppressive agent with improved stability, palatability with high dose of active ingredient. The present invention comprises an active ingredient with other pharmaceutically acceptable excipients such as vehicle, suspending agent, solvent or cosolvent, preservative, sweetener, antifoaming agent, wetting agent, buffering agent and flavouring agent. The present invention also provides a convenient, easy process for preparation thereof.

The present invention provides oral pharmaceutical suspension of an immunosuppressive agent with flavor that has masked unpleasant taste of the drug with patient compliance that eliminates difficulty of administration.

In the present invention, the active pharmaceutical ingredient (API) for oral suspension dosage form is selected from immunosuppressive agent such as azathioprine, mycophenolate mofetil, cyclosporine, fingolimod, methotrexate, leflunomide, cyclophosphamide, chlorambucil, nitrogen mustard, tacrolimus and sirolimus.

In a preferred embodiment of the present invention, the immunosuppressive agent is mycophenolate mofetil.

Mycophenolate mofetil is an immunosuppressant drug used to prevent rejection in organ transplantation. It is a prodrug of mycophenolic acid (MPA). Following oral administration, mycophenolate mofetil is rapidly absorbed and hydrolyzed to mycophenolic acid (MPA). It inhibits an enzyme needed for the growth of T cells and B cells. It reversibly inhibits inosine monophosphate dehydrogenase enzyme that controls the rate of synthesis of guanine monophosphate in the purine_synthesis in the proliferation of B and T lymphocytes.

Mycophenolate mofetil is a broad-spectrum antibiotic and acting as antiviral, antifungal, antibacterial, anticancer, and antipsoriasis. USFDA approved the drug in May 1995 for use in kidney transplantation. Mycophenolate mofetil is marketed under the trade name CellCept.

Mycophenolate mofetil is having an empirical formula of $C_{23}H_{31}NO_7$ and a molecular weight of 433.4947, chemically 2-(morpholin-4-yl)ethyl (4E)-6-(4-hydroxy-6-methoxy-7-methyl-3-oxo-1,3-dihydro-2-benzofuran-5-yl)-4-methylhex-4-enoate, and having the chemical structure as follows:

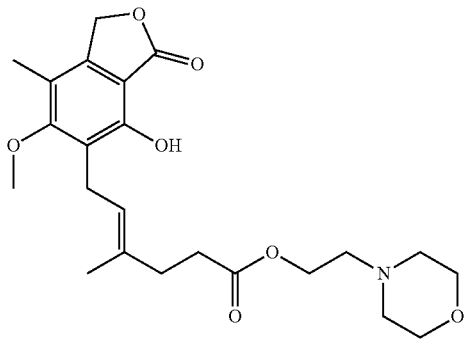 [SMILES: COc1c(C)c2c(c(O)c1C/C=C(\C)CCC(=O)OCCN1CCOCC1)C(=O)OC2]

One aspect of the present invention relates to oral pharmaceutical composition in suspension dosage comprises mycophenolate mofetil as active ingredient and pharmaceutically acceptable excipients. Pharmaceutically acceptable excipients may include vehicle, suspending agent, solvent or cosolvent, preservative, sweetener, antifoaming agent, wetting agent, buffering agent and flavouring agent. The present invention also provides a process for preparation thereof.

Vehicles used in the present pharmaceutical composition are mainly liquid which carry active ingredient and other excipients in dissolved or dispersed state. Pharmaceutical vehicles can be classified as aqueous vehicles and oily vehicles. Aqueous vehicles include water, hydro-alcoholic, polyhydric alcohols and buffers. Oily vehicles include vegetable oils, mineral oils, organic oily bases or emulsified bases. In the present invention, preferably water is used as vehicle.

Suspending agents help active pharmaceutical ingredients stay suspended in the formulation and prevent caking at the bottom of the container. A well-formulated suspension can be easily re-suspended by the use of moderate agitation or shaking. The main suspending agent employed in oral preparations can be selected from but not limited to carrageenan, colloidal silicone dioxide, cellulose ether, xanthan gum, sodium alginate, microcrystalline cellulose. In the present invention, preferably xanthan gum is used as suspending agent.

Solvents or cosolvents are water-miscible organic solvents used in liquid drug formulations to increase the solubility of poorly water soluble substances and enhance the chemical stability of a drug. Solvent or cosolvents can be selected from but not limited to water, ethanol, polyethylene glycols (PEG), sorbitol, glycerin, propylene glycol and benzyl alcohol. In the present invention, preferably glycerin is used as cosolvent to increase solubility of drug.

Preservatives are included in pharmaceutical dosage form and prevent the growth of microorganisms during the product manufacturing and shelf life. Preservatives can be selected from but not limited to benzoic acid, potassium sorbate, sodium benzoate, chlorobutanol, ethanol, butyl paraben, propyl paraben and methyl paraben. In the present invention, preferably methyl paraben and propyl paraben are used as preservatives.

Antifoaming agents are added in oral suspension pharmaceutical dosage form to lower the surface tension and cohesive binding of liquid phase. Antifoaming agents can be selected from but not limited to simethicone, organic phosphates, alcohols, paraffin oils, sterates and glycols. In the present invention, preferably simethicone emulsion is used as antifoaming agent.

Wetting agents are surfactants that lower the interfacial tension and contact angle of solid particles and liquid vehicle in suspensions. Wetting agents can be selected from but not limited to sodium lauryl sulphate, polysorbate 80, spans and lecithins. In the present invention, preferably polysorbate 80 is used as wetting agent as its lacks toxicity and have compatibility with most formulation ingredients.

Buffering agents provide stability and pH control to the pharmaceutical formulations. Buffering agents can be selected from but not limited to sodium acetate, sodium citrate, ammonium sulfate, sodium phosphate, disodium hydrogen phosphate, potassium citrate, citric acid monohydrate, trisodium citrate dihydrate. In the present invention, preferably sodium phosphate buffers are used as buffering agent.

Sweetening agents are added in liquid formulations that impart sweetness and improve patient compliance through taste masking. The main sweetening agents employed in oral preparations can be selected from but not limited to sucrose, liquid glucose, glycerol, sorbitol, saccharin sodium and aspartame. In the present invention, preferably sorbitol is used as sweetener.

Flavoring agents are added to increase patient acceptance of the drug by masking the specific taste sensations. Flavoring agent can be selected but not limited to essential oils including peppermint oil, orange oil, and lemon oil or can be selected from fruit flavors. In the present invention, preferably raspberry flavor is used.

Below table represents the composition of the present invention.

| Sr No | Name of Ingredients | Formula % w/w |
|---|---|---|
| 1 | API | 1-50% |
| 2 | Suspending agent | 1-10% |
| 3 | Cosolvent | 5-30% |
| 4 | Sweetener | 0.01-30% |
| 5 | Preservative | 0.001-1% |
| 6 | Antifoaming agent | 0.001-1% |
| 7 | Wetting agent | 0.001-10% |
| 8 | Buffering agent | 2-20% |
| 9 | Flavouring agent | 0.01-5% |
| 10 | Vehicle | Q.S. |

The oral pharmaceutical suspension of above composition is prepared by following steps but not limited to:
A) Take vehicle and add buffering agent and mix till it get dissolved;
B) Add and mix co-solvent until it get dispersed;
C) Add wetting agent and antifoaming agent one by one and mix till it gets dispersed or dissolved;
D) Add API and mix till it gets dispersed;
E) Add suspending agent, preservative, sweetener, flavouring agent one by one till it dissolved or dispersed;
F) Make volume up to desired batch size.

EXAMPLES

The present invention can be described by way of examples only. They are not to be construed to limit the invention in any manner whatsoever. The following examples are intended to illustrate the various aspects of the invention, though without aiming to limit it.

Below table represents the composition of 1 gm/5 ml mycophenolatemofetil and excipients with its range are shown below:

Example: Oral suspension of mycophenolatemofetil (1 gm/5 ml)

| Sr No | Name of Ingredients | Formula mg/ml |
|---|---|---|
| 1 | Mycophenolatemofetil | 200.0 |
| 2 | Xanthan gum | 2.0 |
| 3 | Glycerin | 100.0 |
| 4 | Sorbitol solution | 100.0 |
| 5 | Sodium methylparaben | 1.8 |
| 6 | Sodium propylparaben | 0.2 |
| 7 | Simethicone emulsion | 10.0 |
| 8 | Polysorbate 80 | 10.0 |
| 9 | NaH2PO4•2H2O | 1.7 |
| 10 | Na2HPO4•2H2O | 16.9 |
| 11 | Raspberry 502700 | 0.2 |
| 12 | Purified water | Q.S. to 1 ml |

The oral pharmaceutical suspension of above composition is prepared by following steps but not limited to:
A) Take vehicle and add buffering agents and mix till it get dissolved;
B) Add and mix co-solvent until it get dispersed;
C) Add wetting agent and antifoaming agent one by one and mix till it gets dispersed or dissolved;
D) Add API and mix till it gets dispersed;
E) Add suspending agent, preservative, sweetener, flavouring agent one by one till it dissolved or dispersed;
F) Make volume up to desired batch size.

We claim:
1. A pharmaceutical composition, comprising:
200 mg/ml of mycophenolate mofetil,
2 mg/ml of xanthan gum,
100 mg/ml of glycerin,
100 mg/ml of sorbitol,
1.8 mg/ml of sodium methylparaben,
0.2 mg/ml of sodium propylparaben,
10 mg/ml of simethicone,
10 mg/ml of polysorbate 80,
1.7 mg/ml of $NaH_2PO_4$ dihydrate,
16.9 mg/ml of $Na_2HPO_4$ dihydrate,
0.2 mg/ml of flavoring agent, and
water.

2. The pharmaceutical composition of claim 1, wherein the flavoring agent comprises an essential oil or a fruit flavor.

3. A process for preparing the pharmaceutical composition of claim 1, wherein the process comprises:
(a) dispensing a first quantity of water, adding the $NaH_2PO_4$ dihydrate and the $Na_2HPO_4$ dihydrate with mixing to obtain a first composition;
(b) adding to the first composition the glycerin with mixing to obtain a second composition;
(c) adding to the second composition the polysorbate 80 and the simethicone emulsion one by one with mixing to obtain a third composition;
(d) adding to the third composition the mycophenolate mofetil with mixing to obtain a fourth composition;
(e) adding to the fourth composition the xanthan gum, the sodium methylparaben, the sodium propylparaben, the sorbitol, and the flavoring agent one by one to obtain a fifth composition; and
adding a second quantity of water to the fifth composition to obtain the pharmaceutical composition.

* * * * *